United States Patent [19]

Nelson

[11] 4,289,127
[45] Sep. 15, 1981

[54] BREATHING APPARATUS STABILIZER

[76] Inventor: Byron G. Nelson, P.O. Box 6457, Lake Charles, La. 70606

[21] Appl. No.: 89,035

[22] Filed: Oct. 29, 1979

[51] Int. Cl.³ .......................................... A61M 15/06
[52] U.S. Cl. ........................ 128/207.14; 128/203.23; 128/136
[58] Field of Search ............. 128/207.14, 136, 205.27, 128/202.21, 203.23, 200.24, 203.12, 203.24, 204.13; 433/91, 140, 93; 131/190, 191

[56] References Cited

U.S. PATENT DOCUMENTS

| | | | |
|---|---|---|---|
| 2,669,988 | 2/1954 | Carpenter | 128/136 |
| 3,106,916 | 10/1963 | Matthes | 128/202.28 |
| 4,170,230 | 10/1979 | Nelson | 128/136 X |

FOREIGN PATENT DOCUMENTS 505545  9/1954  Canada ................................ 433/140

Primary Examiner—Henry J. Recla

[57] ABSTRACT

In a breathing apparatus of the kind which fits inside the mouth in the side of the mouth between the teeth and cheek, being comprised of an elongated air-flow tube which conveys respirated air from the front of the mouth to the rear portion of the mouth proximate the molar teeth, an improvement is disclosed which is defined by a longitudinally extending stabilizing fin affixed to the breathing tube. The stabilizing fin is adapted to fit primarily between the gum and cheek and serves to prevent unwanted expulsion of the breathing apparatus from the mouth and further functions in maintaining the positioning of the air openings of the tube relative to the teeth, cheek and lips of the user of the apparatus.

4 Claims, 8 Drawing Figures

U.S. Patent  Sep. 15, 1981  4,289,127
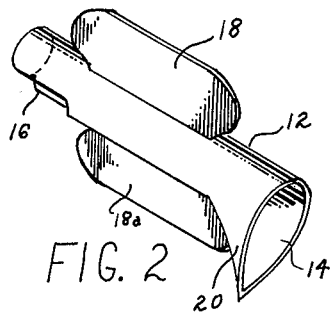
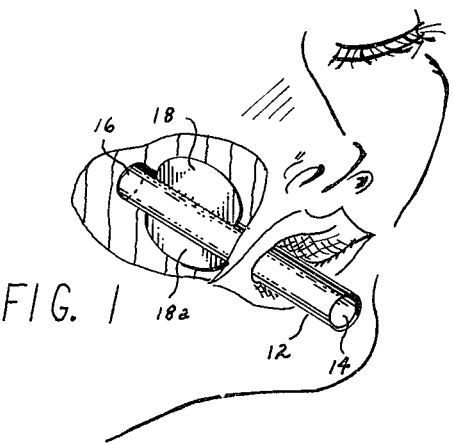
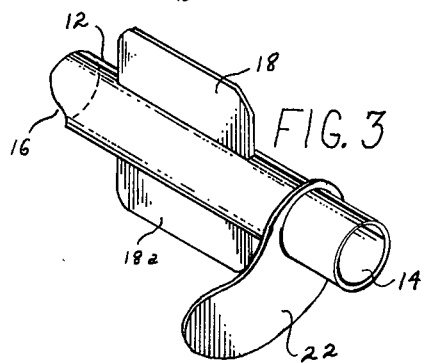
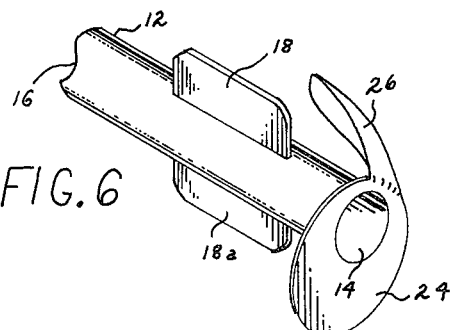
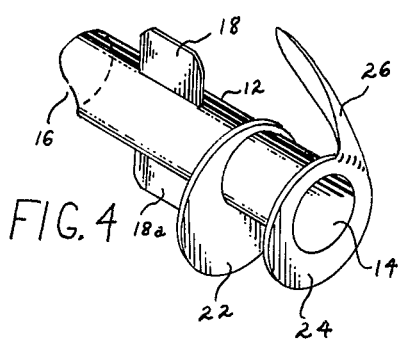
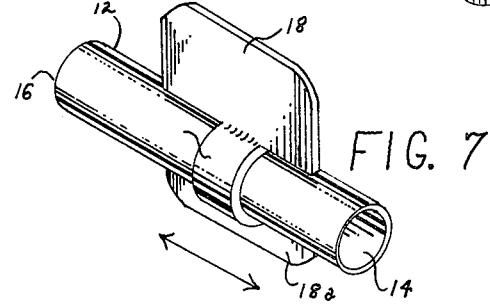
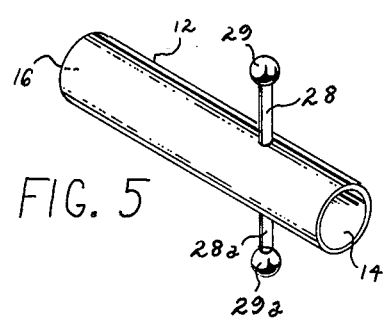
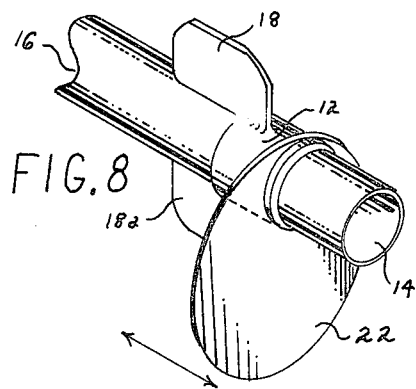

BREATHING APPARATUS STABILIZER

Application Ser. Nos. 97,325 and 99,855 and 88,043 are related cross references.

BACKGROUND OF THE INVENTION

People who use breathing apparatus of the kind which fit inside the mouth in the side of the mouth between the teeth and cheek often have a problem maintaining positioning of the tube of the apparatus so that they may comfortably breath. The tube may slip downward in the mouth to a point between the gum and cheek whereby the air openings of the tube become at least partially blocked by the teeth, the gums, or the lips. Or the apparatus may slip rearward to an extent that the fleshy portion at the rear of the mouth blocks the openings of the tube. Or the apparatus may even rotate within the mouth so as to disorient the direction of the exhaust openings when those openings should face the interior of the mouth. There are times when the apparatus is unwittingly expulsed from the mouth, as during periods of use when sleeping. Also, during periods of sleep, there is always the possibility of swallowing the apparatus of such breathing aids.

It is therefore an object of this invention to provide in a breathing apparatus of the kind described above, means to prevent vertical slippage of the tube of the apparatus between gum and cheek thereby insuring that the air openings will not be blocked by the teeth, gums, or lips.

It is also an object of this invention, while accomplishing the above object to minimize rear slippage of the tube of the breathing apparatus within the mouth to the extent that air flow or saliva drainage will not be impeded by the fleshy portion of the back of the mouth.

It is yet another object of this invention to accomplish the above objects while also preventing unwanted rotation of the tube in the mouth so that by reason of such unwanted rotation lateral air openings become disoriented and air flow is impeded.

It is still another object of this invention to prevent unwanted expulsion of the breathing apparatus from the mouth, especially during times of sleep.

It is yet another object of this invention to lessen the danger of swallowing the apparatus, particularly when the user is asleep.

It is another object of this invention to accomplish the above objects by means that is comfortable to the user of such breathing apparatus.

THE INVENTION

An improvement is disclosed in breathing apparatus of the kind which fit inside the mouth in the side of the mouth between the teeth and cheek, which kind has an elongated air-flow tube having an air intake opening located proximate the lips and an air exhaust opening distal to the lips adjacent the molars, the improvement being a stabilizing means defined by a projecting element affixed to the flow tube of the apparatus and adapted to fit between the gum and cheek.

One embodiment of this invention defines the stabilizing element as being a post-like projection from the flow tube adapted to fit between gum and cheek above or below the tube, being of a length sufficient to prevent unwanted forward or backward movement of the tube or unwanted rotation.

Another embodiment defines the stabilizing element as being a fin-like projection disposed lengthwise the tube, also adapted to fit between cheek and gum and functioning to prevent unwanted movement or rotation of the air-flow tube.

A third embodiment of the invention shows the projecting stabilizing element being snugly coupled to the tube so that there may be longitudinal sliding or rotating adjustment of the stabilizer for comfortable fitment within the mouth.

These and other features of the invention contributing satisfaction in use will be more fully understood when taken in connection with the following description and illustrations in which identical numerals refer to identical parts and in which:

FIG. 1 is a perspective cut-away view of one embodiment of this invention as seen in place in a human mouth;

FIG. 2 is a perspective view of a second embodiment of the invention;

FIG. 3 is a perspective view of a third embodiment of this invention;

FIG. 4 is a perspective view of a fourth embodiment;

FIG. 5 is a perspective view of a fifth embodiment;

FIG. 6 is a perspective view of a sixth embodiment;

FIG. 7 is a perspective view of a seventh embodiment of the invention; and

FIG. 8 is a perspective view of an eighth embodiment of this invention.

Referring now to FIGS. 1-8, it can be seen that all the embodiments of the invention have tube means 12 which tube means 12 has upstream air opening 14 proximate the lips adapted to communicate the atmosphere with the interior of tube means 12. Inhaled air traverses the length of tube means 12 to exit through downstream opening 16. Downstream opening 16 is adapted to communicate the interior of tube means 12 with the rear portion of the mouth at some point adjacent the molars. The length of tube means 12 is sufficient to extend from the front of the mouth back down the side of the mouth between cheek and teeth to the rear portion of that side of the mouth adjacent the molars. Downstream air opening 16 may be adapted to face at least in part the interior of the mouth as can be seen in FIGS. 2, 3, 4, 6, and 8; or downstream air opening 16 may be adapted to face rearward as seen in FIGS. 1, 5, and 7.

FIGS. 1, 2, 3, 4, 6, 7, and 8 show flattened stabilizing fins 18 and 18(a) affixed to the tube means 12. The stabilizing fins 18 and 18(a) is shown as a flattened sheet disposed at some point along the length of tube means 12 so that said stabilizing fins 18 and 18(a) is adapted to fit comfortably between the cheek and gums of the user of the apparatus. Flattened stabilizing fins 18 and 18(a) may be made of any material used in the medical art which is inert in the human mouth, such as latex rubber or plastics. Flattened stabilizing fins 18 and 18(a) may be rigid or flexible, or it may even be malleable so that the user of the breathing apparatus may custom bend stabilizing fin 18 or 18(a) to fit the contours of cheek and gum. Stabilizing fins 18 and 18(a) may be of any length or height or have any perimetrical shape found to be most comfortable in the mouth. Stabilizing fins 18 and 18(a) may be any thickness; in fact, means 18 and 18(a) may be constructed variable in height or thickness along its length.

FIG. 2 shows an embodiment of this invention having flattened stabilizing fins 18 and 18(a) and tube means 12. Tube means 12 at its upstream end is shown somewhat flattened in shape. Flattened upstream end 20 of tube means 12 is adapted to fit between the lips, snugly in the corner of the mouth so that there is an air seal effected when the lips contact flattened upstream end 20.

FIG. 3 shows a third embodiment of this invention having sealing means 22 affixed to tube means 12 and adapted to extend from upstream portion of tube means 12 proximate air opening 14 across the front of the mouth between frontal teeth and lips to an extent to seal off flow of air into the mouth except through upstream opening 14.

FIG. 4 shows a fourth embodiment of the invention having sealing means 22 and external flange stabilizing means 24. External flange stabilizer means 24 is affixed to tube means 12 proximate said opening 14 and adapted to fit externally the lips so as to further stabilize unwanted movement of the apparatus in the mouth. Attached to flange means 24 is an additional curved portion 26 which is adapted to follow the contours of the outer cheek thereby lessening the possibility of swallowing the device.

FIG. 5 shows stabilizing means 28 and 28(a) as a rod with ball on the end 29 and 29(a). Stabilizing rods 28 and 28(a) are adapted to fit between the cheek and gum, and function to prevent rotation of the apparatus or expulsion of the apparatus from the mouth, as well as to position the apparatus in the mouth. Stabilizing rods 28 and 28(a) may be made of any material, like fins 18 and 18(a), but are best suited to be malleable, as with a wire, so that rods 28 and 28(a) may be bent for adjustment to the contours of the inner cheek and gums. Like flattened stabilizing fins 18 and 18(a), rod 28 and 28(a) may be any workable length or thickness and may be situated anywhere along the length of tube means 12 so long as rod 28 and 28(a) remain in the area between cheek and gum. Ball 29 and 29(a) function to improve comfort to the user, however, ball 29 and 29(a) are not entirely necessary when rod 28 and 28(a) are sufficiently blunt. The drawing shows one stabilizing rod 28 which fits between the cheek and upper jaw gum and one stabilizer rod 28(a) which fits between lower cheek and jaw gum; it is to be understood, however, that depending upon the positioning in the mouth the user wants the breathing apparatus to be, there may be only one rod stabilizer 28 or 28(a) situated anywhere along the length of tube means 12 either above or below tube means 12, or a plurality of stabilizers 28, 28(a), as for instance, when stabilizer rod 28, 28(a) be situated at both the upstream portion and the downstream portion of tube means 12.

FIG. 6 shows tube means 12 having attached to the upstream portion proximate upstream opening 14, flange stabilizing means 24 and arm 26.

FIG. 7 shows flattened stabilizing fins 18 and 18(a) affixed to moveable coupling 32 so that flattened stabilizing fin 18, 18(a) may be slidably adjustable along the length of tube means 12.

FIG. 8 shows flattened stabilizer 18, 18(a) affixed to moveable coupling 34. Attached to moveable coupling 34 is also sealing means 22. The user of this embodiment of the invention can slidably adjust along the length of tube means 12 the fit of both sealing means 22 and flattened stabilizer 18, 18(a) with the same physical motion.

Tube means 12 is shown in a primarily cylindrical shape in the drawings, but it is to be understood that tube means 12 may be any shape as taken transverse the long axis which is considered comfortable and functional.

The drawings of FIGS. 1, 2, 3, 4, 6, 7, and 8 show flattened stabilizing fins 18, 18(a) adapted for fitment between cheek and upper and lower jaw gums. It should be understood that the apparatus may be made with only one stabilizing fin 18, without stabilizing fin 18(a), and vice-versa for those with peculiar mouth problems requiring either of the above mentioned modes, as for instance, during times of oral surgery.

The invention may be made by molding, injection molding, extruding, and the like methods of manufacture. It may be constructed of any material which is inert in the human mouth, such as latex rubber or plastics used in the medical or dental profession.

It can be seen from the above discussion that the stabilizing means of this invention serves to inhance comfort and safety to the user thereor as well as provides for unobstructed air flow by maintaining position of the breathing apparatus in the mouth.

What is claimed is:

1. In a breathing apparatus of the kind which fits inside the mouth of a human between cheek and teeth, which kind has tube means for air flow, said tube means having at least one upstream air opening proximate the lips, said tube means adapted and being of a length sufficient to extend from the front of the mouth back down the side of the mouth between cheek and teeth to the rear of the mouth adjacent the molars, said tube means having at least one downstream air opening adapted to communicate the interior of said tube means with said rear of said mouth, said downstream air opening being located at a point adjacent the molars, with said upstream opening in combination with said downstream opening being sized to permit a flow of respirated air through said tube means approximate the flow of air said human could achieve through normal nasal breathing; an improvement comprising stabilizing means affixed and extending laterally from said tube means, said stabilizing means being adapted to fit between the cheek and jaw gum and adapted to contact the jaw gum.

2. The improvement of claim 1 wherein said stabilizing means is a fin-like projection from said tube means.

3. The improvement of claim 1 wherein said stabilizing means is moveable along the length of said tube means.

4. In a breathing apparatus of the kind which fits inside the mouth of a human between cheek and teeth, which kind has tube means for air flow, said tube means having at least one upstream opening proximate the lips, said tube means being adapted and of a length sufficient to extend from the front of the mouth back down the side of the mouth between cheek and teeth to the rear of the mouth adjacent the molars, said tube means having at least one downstream air opening adapted to communicate the interior of said tube means with said rear of said mouth, said downstream air opening being located at a point adjacent the molars, with said upstream air opening in combination with said downstream opening being sized to permit a flow of respirated air through said tube means approximate the flow of air said human could achieve through normal nasal breathing; an improvement comprising wire-like stabilizing means affixed to and extending laterally from said tube means, said wire-like stabilizing means being adapted to fit between the cheek and jaw gum and adapted to contact the jaw gum.

* * * * *